United States Patent
Kumar

(10) Patent No.: US 11,213,288 B2
(45) Date of Patent: Jan. 4, 2022

(54) PORT SITE CLOSURE INSTRUMENT

(71) Applicant: Covidien LP, Mansfield, MA (US)

(72) Inventor: Neeraj Kumar, Noida (IN)

(73) Assignee: Covidien LP, Mansfield, MA (US)

( * ) Notice: Subject to any disclaimer, the term of this patent is extended or adjusted under 35 U.S.C. 154(b) by 366 days.

(21) Appl. No.: 16/364,569

(22) Filed: Mar. 26, 2019

(65) Prior Publication Data

US 2019/0336123 A1 Nov. 7, 2019

Related U.S. Application Data

(60) Provisional application No. 62/665,577, filed on May 2, 2018.

(51) Int. Cl.
*A61B 17/04* (2006.01)
*A61B 17/06* (2006.01)

(52) U.S. Cl.
CPC ...... *A61B 17/0482* (2013.01); *A61B 17/0469* (2013.01); *A61B 17/0485* (2013.01); *A61B 17/06066* (2013.01); *A61B 17/06004* (2013.01); *A61B 17/06114* (2013.01); *A61B 2017/06085* (2013.01)

(58) Field of Classification Search
CPC ............ A61B 17/0482; A61B 17/0469; A61B 17/06066; A61B 17/0485
See application file for complete search history.

(56) References Cited

U.S. PATENT DOCUMENTS

| | | |
|---|---|---|
| 5,499,997 A | 3/1996 | Sharpe et al. |
| 5,507,757 A | 4/1996 | Sauer et al. |
| 5,507,758 A | 4/1996 | Thomason et al. |
| 5,527,343 A | 6/1996 | Bonutti |
| 5,653,716 A | 8/1997 | Malo et al. |
| 5,716,369 A | 2/1998 | Riza |
| 5,817,111 A | 10/1998 | Riza |

(Continued)

FOREIGN PATENT DOCUMENTS

| | | |
|---|---|---|
| EP | 2305151 A1 | 4/2011 |
| EP | 2412317 A1 | 2/2012 |

(Continued)

OTHER PUBLICATIONS

European Search Report dated Oct. 9, 2019 issued in EP Appln. No. 19172129, 8 pages.

*Primary Examiner* — Tuan V Nguyen

(57) ABSTRACT

A port site closure instrument includes a pair of wings and a body having proximal, central, and distal portions. The proximal portion defines a proximal suture aperture and first and second needle apertures. The central portion defines third and fourth needle apertures. A first needle channel is defined through the body communicating the first and third needle apertures. A second needle channel is defined through the body communicating the second and fourth needle apertures. The distal portion defines distal suture apertures. A first suture channel is defined by the body communicating the proximal and distal suture apertures. The pair of wings is pivotally supported by the distal portion of the body. Each of the wings define a suture slot such that a suture exiting one of the distal suture apertures and positioned in the suture slots is aligned with one of the first or second needle channels.

20 Claims, 8 Drawing Sheets

(56) References Cited

U.S. PATENT DOCUMENTS

| | | |
|---|---|---|
| 5,846,253 A | 12/1998 | Buelna et al. |
| 5,860,991 A | 1/1999 | Klein et al. |
| 5,868,762 A | 2/1999 | Cragg et al. |
| 5,899,911 A | 5/1999 | Carter |
| 5,902,311 A | 5/1999 | Andreas et al. |
| 5,948,001 A | 9/1999 | Larsen |
| 5,972,005 A | 10/1999 | Stalker et al. |
| 5,993,471 A | 11/1999 | Riza et al. |
| 5,993,474 A | 11/1999 | Ouchi |
| 6,022,360 A | 2/2000 | Reimels et al. |
| 6,036,699 A | 3/2000 | Andreas et al. |
| 6,059,800 A | 5/2000 | Hart et al. |
| 6,099,550 A | 8/2000 | Yoon |
| 6,110,184 A | 8/2000 | Weadock |
| 6,136,010 A | 10/2000 | Modesitt et al. |
| 6,245,079 B1 | 6/2001 | Nobles et al. |
| 6,245,080 B1 | 6/2001 | Levinson |
| 6,296,648 B1 | 10/2001 | Boche et al. |
| 6,355,050 B1 | 3/2002 | Andreas et al. |
| 6,398,796 B2 | 6/2002 | Levinson |
| 6,491,707 B2 | 12/2002 | Makower et al. |
| 6,500,184 B1 | 12/2002 | Chan et al. |
| 6,517,553 B2 | 2/2003 | Klein et al. |
| 6,551,331 B2 | 4/2003 | Nobles et al. |
| 6,743,241 B2 | 6/2004 | Kerr |
| 6,770,084 B1 | 8/2004 | Bain et al. |
| 6,896,685 B1 | 5/2005 | Davenport |
| 6,939,357 B2 | 9/2005 | Navarro et al. |
| 7,004,952 B2 | 2/2006 | Nobles et al. |
| 7,048,749 B2 | 5/2006 | Kortenbach et al. |
| 7,090,686 B2 | 8/2006 | Nobles et al. |
| 7,291,155 B2 | 11/2007 | Batke et al. |
| 7,449,024 B2 | 11/2008 | Stafford |
| 7,462,188 B2 | 12/2008 | McIntosh |
| 7,601,161 B1 | 10/2009 | Nobles et al. |
| 7,722,629 B2 | 5/2010 | Chambers |
| 7,736,388 B2 | 6/2010 | Goldfarb et al. |
| 7,824,419 B2 | 11/2010 | Boraiah |
| 7,850,701 B2 | 12/2010 | Modesitt et al. |
| 8,038,687 B2 | 10/2011 | Pipenhagen et al. |
| 8,172,860 B2 | 5/2012 | Zung et al. |
| 8,211,122 B2 | 7/2012 | McIntosh |
| 8,317,679 B2 | 11/2012 | Surti |
| 8,348,962 B2 | 1/2013 | Nobles et al. |
| 8,926,639 B2 * | 1/2015 | Bagaoisan ......... A61B 17/0482 606/144 |
| 9,675,342 B2 | 6/2017 | Prior et al. |
| 2002/0016614 A1 | 2/2002 | Klein et al. |
| 2002/0049453 A1 | 4/2002 | Nobles et al. |
| 2003/0009180 A1 | 1/2003 | Hinchliffe et al. |
| 2003/0028201 A1 | 2/2003 | Navarro et al. |
| 2004/0092964 A1 | 5/2004 | Modesitt et al. |
| 2004/0098047 A1 | 5/2004 | Frazier et al. |
| 2004/0186487 A1 | 9/2004 | Klein et al. |
| 2004/0199185 A1 | 10/2004 | Davignon |
| 2004/0225301 A1 | 11/2004 | Roop et al. |
| 2005/0119670 A1 | 6/2005 | Kerr |
| 2005/0212221 A1 | 9/2005 | Smith et al. |
| 2006/0030868 A1 * | 2/2006 | Bennett, III ....... A61B 17/0482 606/148 |
| 2006/0195120 A1 | 8/2006 | Nobles et al. |
| 2007/0088247 A1 | 4/2007 | Bliweis et al. |
| 2007/0203507 A1 | 8/2007 | McLaughlin et al. |
| 2007/0250112 A1 | 10/2007 | Ravikumar et al. |
| 2008/0033459 A1 | 2/2008 | Shafi et al. |
| 2008/0097480 A1 | 4/2008 | Schorr et al. |
| 2008/0097481 A1 | 4/2008 | Schorr et al. |
| 2008/0097486 A1 * | 4/2008 | Ross ................. A61B 17/1671 606/151 |
| 2008/0255592 A1 | 10/2008 | Hsu et al. |
| 2010/0012152 A1 | 1/2010 | Hansen |
| 2010/0262166 A1 | 10/2010 | Boraiah et al. |
| 2011/0082475 A1 * | 4/2011 | Smith ................ A61B 17/0057 606/144 |
| 2011/0237901 A1 | 9/2011 | Duke et al. |
| 2011/0270282 A1 | 11/2011 | Lemke |
| 2011/0313433 A1 | 12/2011 | Woodard, Jr. et al. |
| 2012/0010634 A1 | 1/2012 | Crabb et al. |
| 2012/0029532 A1 | 2/2012 | Hodgkinson et al. |
| 2012/0143221 A1 | 6/2012 | Weisel et al. |
| 2012/0191109 A1 | 7/2012 | Rockrohr |
| 2013/0012962 A1 | 1/2013 | Stone |
| 2013/0079597 A1 | 3/2013 | Auerbach et al. |
| 2013/0165956 A1 | 6/2013 | Sherts et al. |
| 2015/0038800 A1 | 2/2015 | Prior et al. |
| 2017/0112481 A1 * | 4/2017 | Bagaoisan ......... A61B 17/0491 |
| 2019/0000506 A1 * | 1/2019 | Parihar .............. A61B 17/3474 |

FOREIGN PATENT DOCUMENTS

| | | |
|---|---|---|
| EP | 2547270 A1 | 1/2013 |
| WO | 9502998 A1 | 2/1995 |
| WO | 2006111955 A2 | 10/2006 |
| WO | 2011128392 A1 | 10/2011 |
| WO | 2012093094 A1 | 7/2012 |
| WO | 2013105993 A2 | 7/2013 |

* cited by examiner

PORT SITE CLOSURE INSTRUMENT

CROSS-REFERENCE TO RELATED APPLICATION

This application claims the benefit of and priority to U.S. Provisional Patent Application No. 62/665,577 filed May 2, 2018, the entire disclosure of which is incorporated by reference herein.

BACKGROUND

1. Technical Field

The present disclosure relates to surgical instruments and, more specifically, port site closure instruments.

2. Discussion of Related Art

Laparoscopic surgical procedures have many advantages over open surgical procedures. One advantage is that laparoscopic surgical procedures generally impose reduced trauma, less risk of infection, and require shorter hospital stays when compared to open surgical procedures.

Laparoscopic surgical procedures are typically performed through one or more incisions in abdominal tissue to access the abdominal cavity underlying the abdominal tissue. In some surgical laparoscopic procedures, a port may be inserted into one or more of the incisions to keep the incision(s) open during the surgical procedure.

After the surgical procedure is completed, the incision or port site incision must be closed in such a way that a fascia layer/rectus sheath of the abdominal tissue is secured together. Generally, closing the fascia layer/rectus sheath of the tissue involves introducing a curved suture needle into the port site incision to grasp the abdominal tissue, especially the fascia layer. However, passing the suture needle through the incision can cause the suture needle to contact organs within the abdominal cavity. In addition, in some patients, e.g., obese patients, the incision size may need to be increased to allow the suture needle to grasp the fascia layer.

Suture passers are known which assist a surgeon in closing a port site incision. However, the suture passers generally require the surgeon to feed the suture into the suture passer through a second incision in the abdominal tissue.

A continuing need exist in the surgical arts for an instrument that can close a port site incision without creating additional incisions in the patient while minimizing the risk of injury to the patient.

SUMMARY

This disclosure relates generally to a port site closure instrument that can be inserted into an incision and pass a suture through tissue to close the incision. The port site closure instrument allows the suture and needles to be passed through same incision that the port site closure instrument is passed through such that the incision can be closed. Further, the port site closure instrument can protect organs underlying the tissue from being contacted by needles used to draw the suture through the tissue.

In an aspect of the present disclosure, a port site closure instrument includes a body and a pair of wings. The body defines a central longitudinal axis, a first plane, and a second plane that is perpendicular to the first plane. The first and second planes intersect along the central longitudinal axis. The body has a proximal portion, a central portion, and a distal portion. The proximal portion defines a first proximal suture aperture, a first needle aperture, and a second needle aperture. The first and second needle apertures are offset from the central longitudinal axis. The central portion defines a third needle aperture and a fourth needle aperture. A first needle channel is defined through the body which communicates the third needle aperture with the first needle aperture. A second needle channel is defined through the body which communicates the fourth needle aperture with the second needle aperture. The first and second needle channels are positioned in the first plane. The distal portion defines distal suture apertures in the first plane on opposite sides of the central portion. The first suture channel is defined by the body which communicates the distal suture apertures with the first proximal suture aperture. The pair of wings is pivotally supported by the distal portion of the body. The pair of wings is pivotable between an open position and a closed position. An outer surface of each of the wings defines a suture slot that is positioned along the first plane such that a suture exiting a respective one of the distal suture apertures and positioned in the suture slots is aligned with a respective one of the first or second needle channels.

In aspects, each of the first and second needle channels is configured to receive a needle and to align the needle with a suture slot of a respective one of the wings. Each of the wings may define a needle slot proximal of the suture slot. The needle slot may be configured to receive a distal end of the needle and to protect the needle from extending through the wing when the wing is in the open position.

In some aspects, the pair of wings is biased toward the open position. Each wing of the pair of wings may have a blunt tip that is configured to atruamatically contact tissue. The instrument may include a pivot pin that passes through each of the wings and the distal portion of the body to pivotally couple the pair of wings to the distal portion. The instrument may include a torsion spring disposed about the pivot pin that is engaged with each of the pair of wings to bias the pair of wings towards the open position.

In certain aspects, the proximal portion of the body defines a second proximal suture aperture. A second suture channel defined by the body may communicate the distal suture apertures with the second proximal suture aperture. The first and second suture channels may be on opposite sides of the central longitudinal axis proximal of the third and fourth needle apertures and may form a common suture channel along the central longitudinal axis distal of the third and fourth needle apertures.

In particular aspects, the first suture channel extends along the second plane and is offset from the central longitudinal axis proximal of the third and fourth needle apertures. A segment of the first suture channel may extend along the central longitudinal axis distal of the third and fourth needle apertures.

In aspects, the distal portion includes a suture passage that extends directly between the distal suture apertures and perpendicular to the central longitudinal axis. The first and second needle channels may intersect one another at the central longitudinal axis.

In another aspect of the present disclosure, a port site closure system includes a needle, a suture, and a port site closure instrument. The suture has first and second ends. The port site closure instrument includes a body and a pair of wings. The body defines a central longitudinal axis, a first plane, and a second plane that is perpendicular to the first plane. The first and second planes intersect along the central longitudinal axis. The body includes a proximal portion, a central portion, and a distal portion. The proximal portion defines a first proximal suture aperture, a first needle aperture, and a second needle aperture. The first and second needle apertures are offset from the central longitudinal axis. The central portion defines a third needle aperture and a fourth needle aperture. A first needle channel is defined through the body which communicates the third needle aperture with the first needle aperture. A second needle channel is defined through the body which communicates the fourth needle aperture with the second needle aperture. The first and second needle channels are positioned in the first plane. The needle is configured to slide through each of the first and second needle channels. The distal portion defines distal suture apertures in the first plane on opposite sides of the central portion. The first suture channel is defined by the body which communicates the distal suture apertures with the first proximal suture aperture. The pair of wings is pivotally supported by the distal portion of the body. The pair of wings is pivotable relative to one another between an open position and a closed position. The outer surface of each of the wings defines a suture slot that is positioned along the first plane. The suture passes through the first suture channel, exits one of the distal suture apertures, and is disposed within the suture slot of each of the wings such that the suture is aligned with a respective one of the first and second needle channels.

In aspects, each of the first and second needle channels is configured to receive the needle and to align the needle with a portion of the suture extending between one of the distal suture apertures and a respective one of the suture slots. The suture may be configured to draw the pair of wings towards the closed position.

In another aspect of the present disclosure, a method of closing an incision in tissue of a patient includes passing a distal portion of a port site closure instrument through the incision and into a body cavity with a pair of wings coupled to the distal portion of the port site closure instrument in a closed position to position the pair of wings within a body cavity of the patient. When the pair of wings are within the body cavity, the pair of wings are allowed to transition to an open position with a proximal portion of the port site closure instrument positioned on an opposite side of the tissue from the distal portion of the port site closure instrument. The method includes passing a needle through a first needle channel of the port site closure instrument such that the needle captures a first portion of a loop of a suture that is disposed on the pair of wings and extends from a pair of distal suture apertures disposed on opposite sides of the distal portion of the port site closure instrument. The needle is withdrawing thought first needle channel to draw the first portion of the loop of the suture through the first needle channel. The needle is then passed through the second needle channel of the port site closure instrument such that the needle captures a second portion of the loop of the suture. The needle is then withdrawn through the second needle channel to draw the second portion of the loop of the suture through the second needle channel. The port site closure instrument is then removed from the incision and first and second ends of the suture are drawn proximally to close the incision.

In aspects, passing the needle through the first needle channel includes the needle passing through tissue between the port site closure instrument and the first portion of the suture. The needle may pass through an inner-most layer of the tissue, e.g., fascia layer/rectus sheath of the tissue. Withdrawing the needle to draw the first portion of the loop of the suture through the first needle channel may include drawing the first portion of the suture and the first end of the suture through the tissue including the inner-most layer of the tissue.

In some aspects, the method may include drawing the first and second ends of the suture proximally such that the suture holds the pair of wings in the closed position while passing the distal portion of the port site closure instrument the incision into the body cavity. Allowing the pair of wings to transition to the open position within the body cavity may include releasing the first and second ends of the suture to allow the pair of wings to transition to the open position. The pair of wings may be biased towards the open position.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION OF EMBODIMENTS

Figure 1:
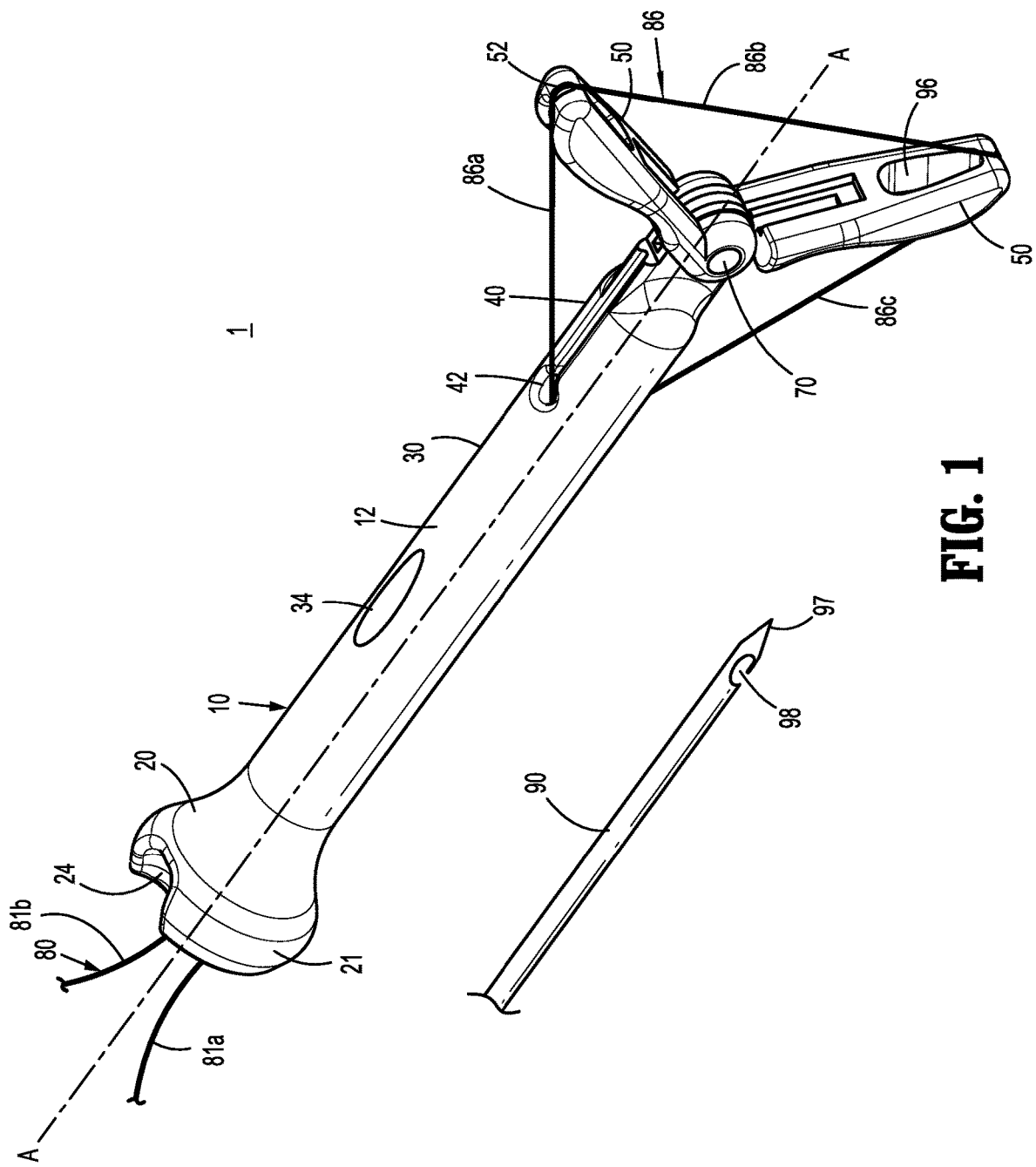
FIG. 1 is a front perspective view of an exemplary embodiment of a port site closure system provided in accordance with the present disclosure including a port site closure instrument, a suture, and a needle, the port site closure instrument having wings in an open position.

Embodiments of the presently disclosed port site closure system are now described in detail with reference to the drawings in which like reference numerals designate identical or corresponding elements in each of the several views. As used herein, the term "clinician" refers to a doctor, a surgeon, a nurse, or any other care provider and may include support personnel. Throughout this description, the term "proximal" refers to the portion of the device or component thereof that is closer to the clinician and the term "distal" refers to the portion of the device or component thereof that is farther from the clinician.

This disclosure relates generally to a port site closure system including a port site closure instrument, a needle, and a suture. The port site closure instrument is configured to pass through a port site incision in tissue and includes a pair of wings that support the suture and first and second channels. The first and second channels are positioned in the instrument to align the needle with the suture such that the needle can grasp and withdraw the suture through tissue on opposite sides of the incision and through the first and second channels to close the incision.

Figure 2:
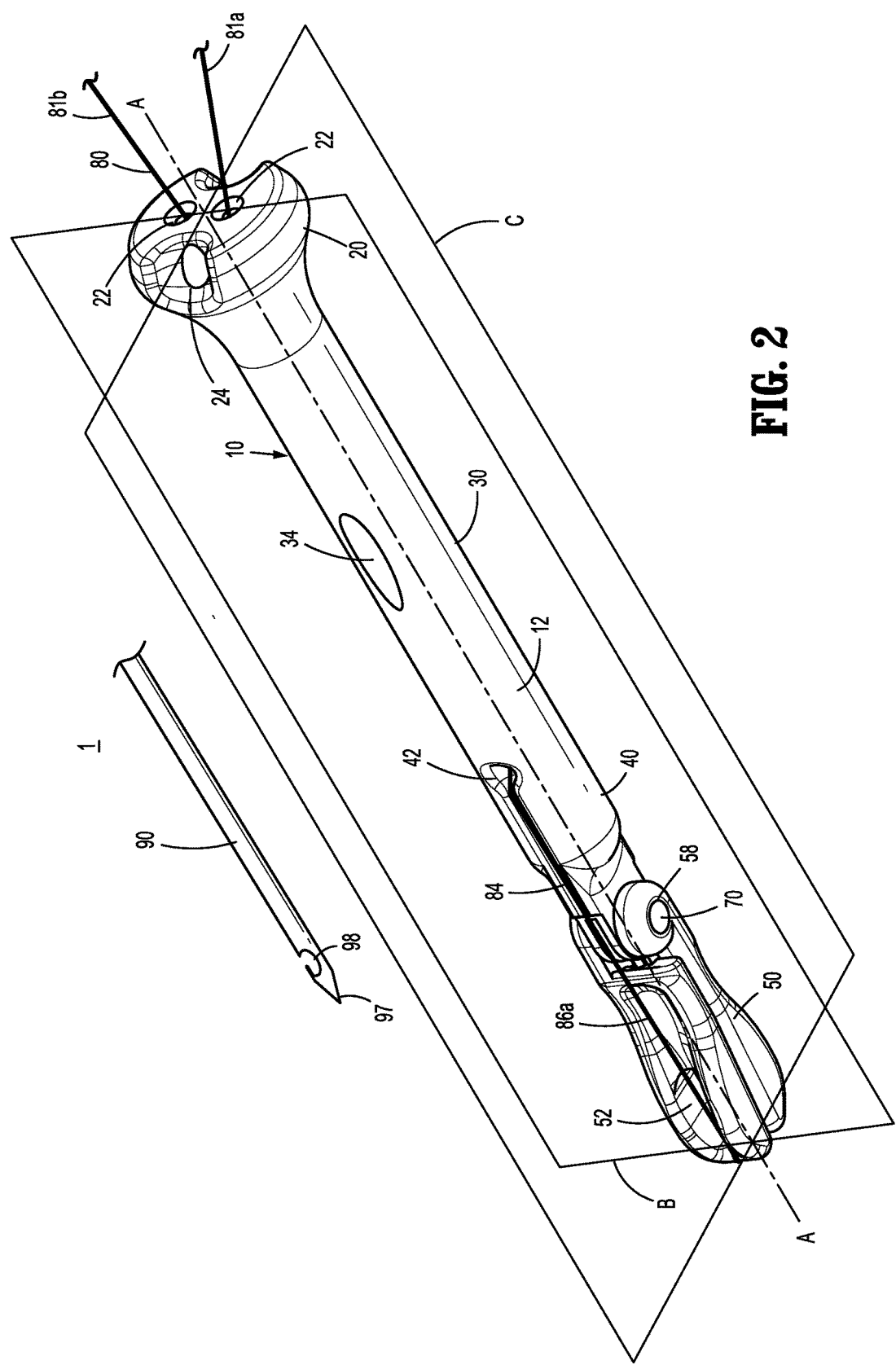
FIG. 2 is a rear perspective view of the port site closure system of FIG. 1 with the wings of the port site closure instrument in a closed position.

Referring now to FIGS. 1 and 2, a port site closure system 1 is provided in accordance with the present disclosure and includes a port site closure instrument 10, a suture 80, and a needle 90. The port site closure system 1 may be provided as a kit that is sterilized and packaged with or without the suture 80 for use during a surgical procedure.

Figure 6:
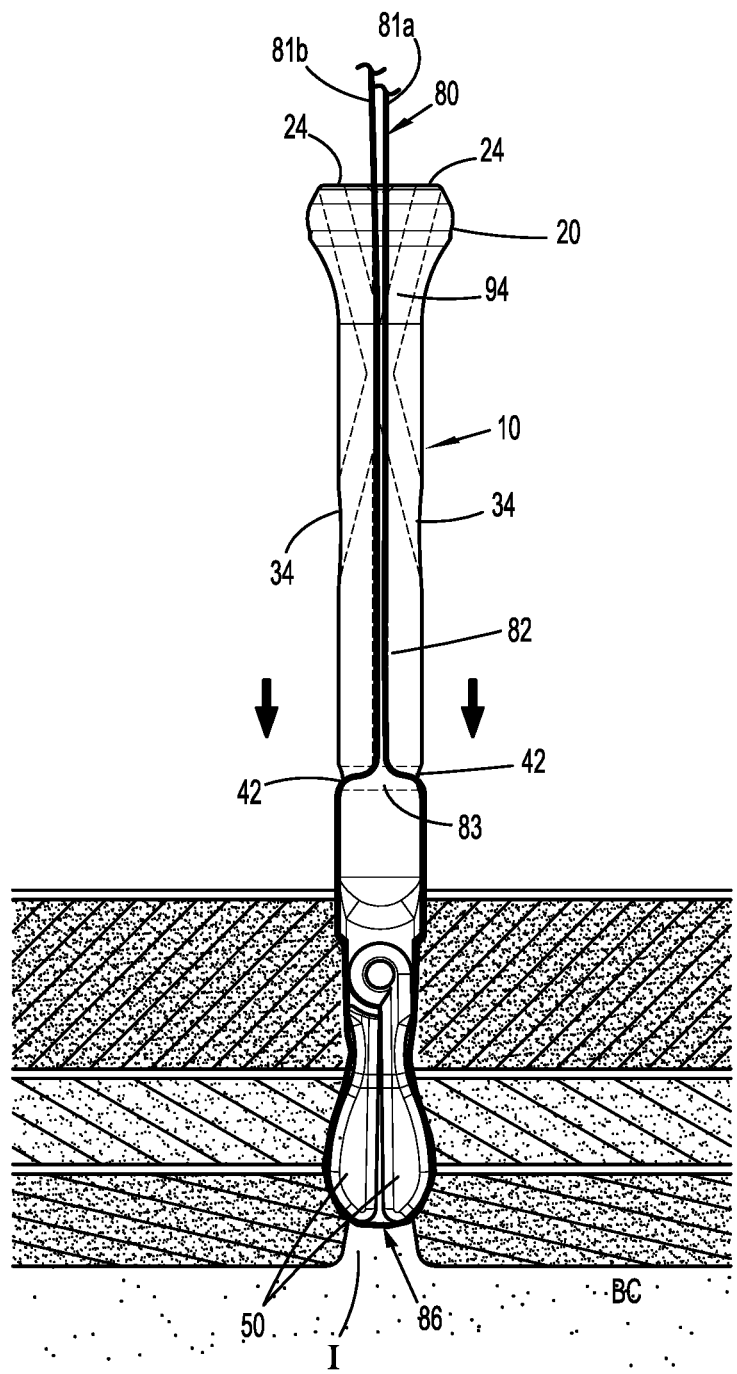
FIG. 6 is a side view of the port site closure instrument and suture of FIG. 1 positioned within an incision in tissue with the wings in the closed position.

The port site closure instrument 10 includes a body 12 having a proximal portion 20, a central portion 30, and a distal portion 40. The port site closure instrument 10 also includes wings 50 supported by the distal portion 40. The body 12 defines a longitudinal axis A-A. In embodiments, the proximal portion 20 includes a flange 21 that has a diameter that is greater than the diameter of the central portion 30. The flange 21 may be dimensioned obstruct passage of the proximal portion 20 of the port site closure instrument 10 into an opening, e.g., incision I (FIG. 6). With particular reference to FIG. 2, the proximal portion 20 defines proximal suture apertures 22 and proximal needle apertures 24. In some embodiments, the proximal suture apertures 22 are disposed in a plane B that includes the longitudinal axis A-A and center points of the proximal suture apertures 22. The center points of the proximal needle apertures 24 are disposed in a plane C that extends through the longitudinal axis A-A and is orthogonal to the plane B.

Figure 3:
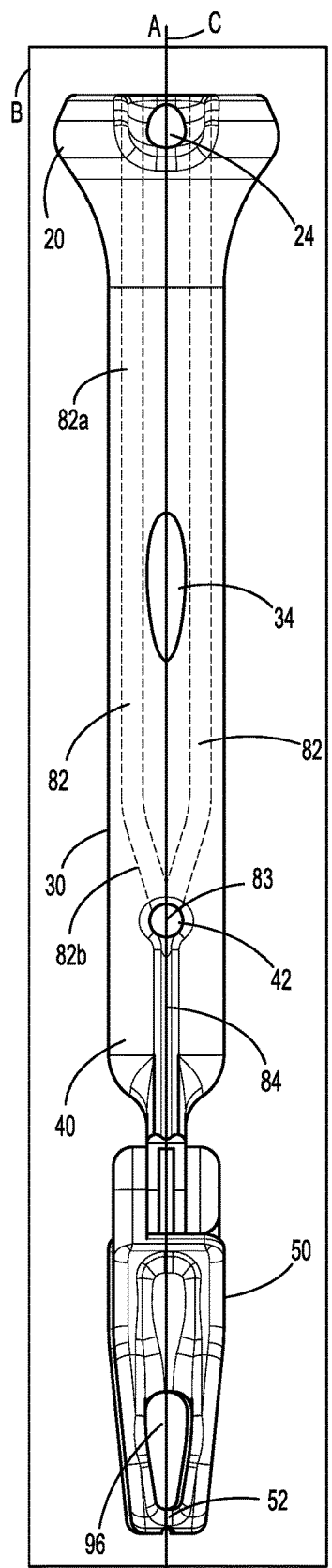
FIG. 3 is a top view of the port site closure instrument of FIG. 1 with the wings in the closed position.
Figure 4:
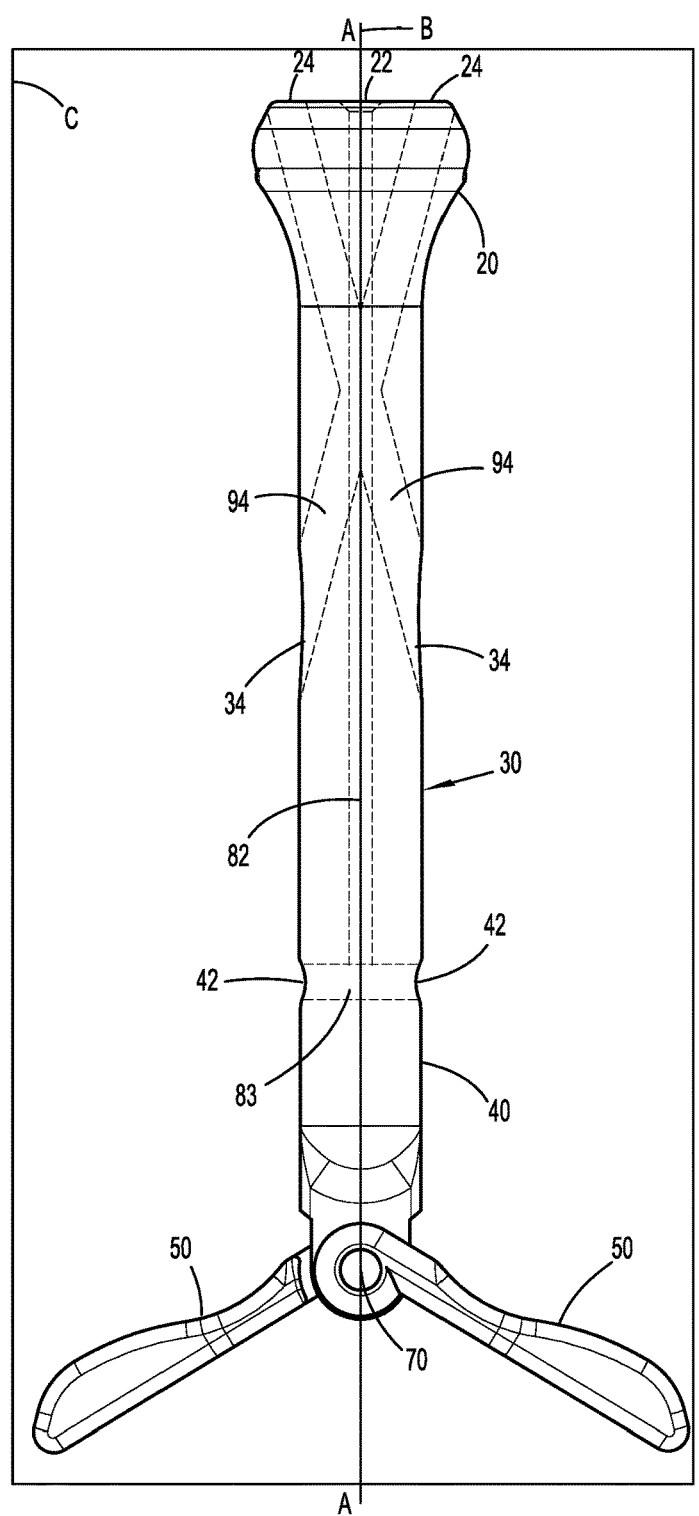
FIG. 4 is a side view of the port site closure instrument of FIG. 1 with the wings in the open position.

With reference to FIGS. 2-4, the central portion 30 of the port site closure instrument 10 defines suture channels 82 that extend between the proximal suture apertures 22 and the distal suture apertures 42. The distal suture apertures 42 extend in a direction radially outwardly of the longitudinal axis A-A. In some embodiments, the distal suture apertures 42 extend in a direction that is perpendicular to the longitudinal axis A-A such that the distal suture apertures 42 are in plane C and radially aligned with the proximal needle apertures 24. The distal suture apertures 42 extend through the distal portion 40 of the port site closure instrument 10 such that a distal suture passage 83 (FIG. 4) is defined directly between the distal suture apertures 42.

With particular reference to FIG. 3, the suture channels 82 have a proximal section 82a and a distal section 82b. The proximal section 82a extends in a direction parallel to the longitudinal axis A-A and the distal section 82b of the suture channels 82 extends from the proximal section 82a of a respective suture channel 82 to the distal suture passage 83. The distal sections 82b may intersect before the distal suture passage 83.

As shown, the body 12 defines two suture channels 82 that extend between the proximal suture apertures 22 and the distal suture apertures 42; however, it is envisioned that that body 12 may define a single suture channel 82 from a single proximal suture aperture 22. In such an embodiment, the single suture channel 82 would be in communication with the distal suture passage 83 to allow the suture 80 to extend from each of the distal suture apertures 42.

The distal portion 40 of the body 12 of the port site closure instrument 10 defines suture grooves 84 (FIG. 3) in an outer surface thereof that extend from the distal suture apertures 42 in a direction parallel to the longitudinal axis A-A and in plane C. The suture grooves 84 are radially aligned with the proximal needle apertures 24.

With reference to FIGS. 2-4, each of the proximal needle apertures 24 communicates with the distal needle aperture 34 on the opposite side of the port site closure instrument 10 by a respective needle channel 94. Each of the needle channels 94 is sized to receive the needle 90 (FIG. 1) such that the needle 90 is movable within plane C. The distal needle apertures 34 are defined in the central portion 30 of the port site closure instrument 10 between and radially aligned with a proximal needle aperture 24 and a distal suture aperture 42 such that a needle 90 passed through one of the needle channels 94 intersects an axis defined by the distal suture passage 83 that extends between the distal suture apertures 42. The needle channels 94 are positioned along plane C and form an "X" between the proximal needle apertures 24 and the distal needle apertures 34 such that the needle channels 94 are in communication with one another.

Figure 5:
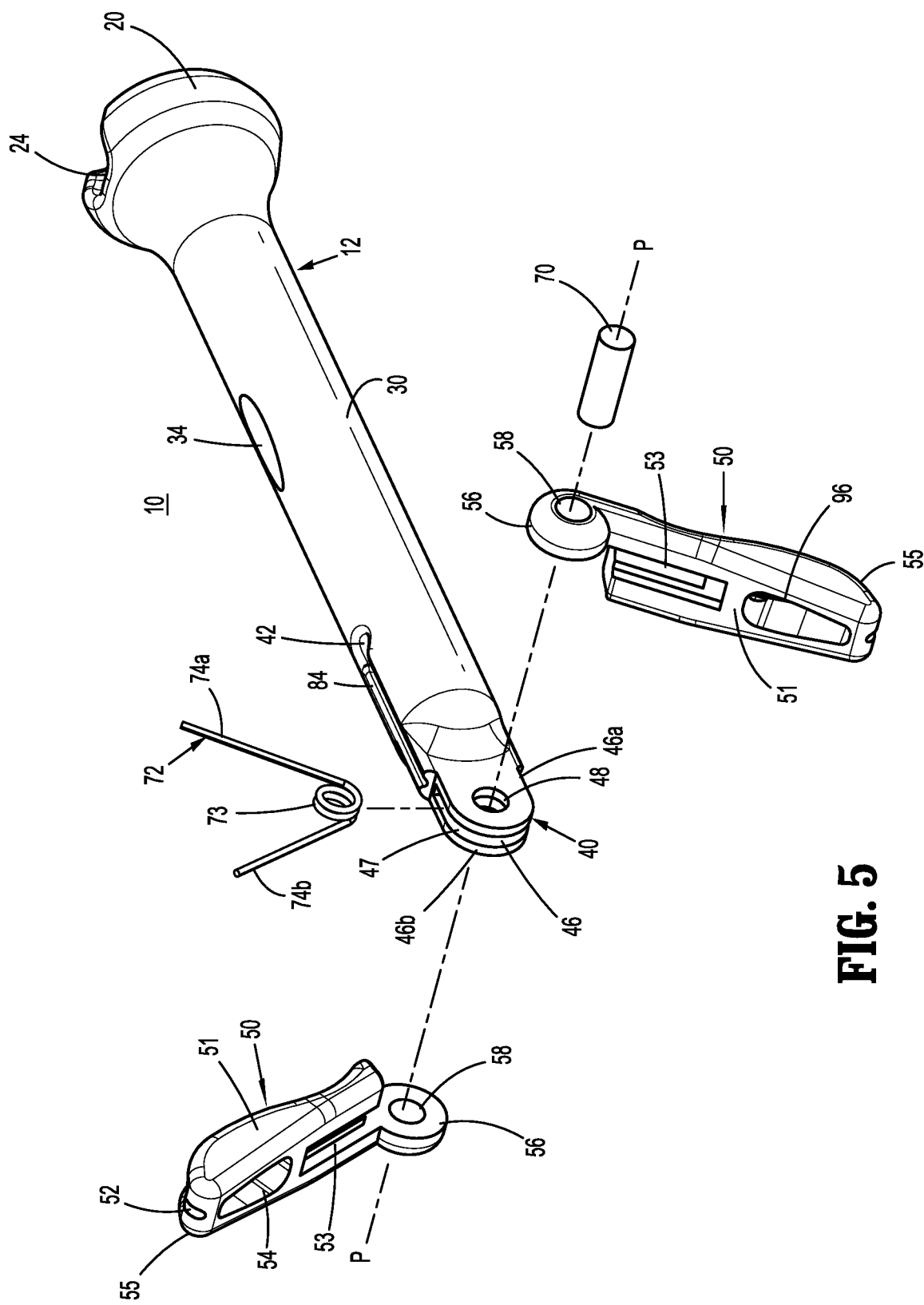
FIG. 5 is front perspective view, with parts separated, of the port site closure instrument of FIG. 1.

Referring to FIG. 5, the distal portion 40 of the port site closure instrument 10 includes a wing support 46 that extends distally beyond the distal suture apertures 42 of the body 12. The wing support 46 defines a pivot pin opening 48 that is transverse to the longitudinal axis A-A. The wing support 46 may include first and second tines 46a, 46b that define a gap 47 therebetween. The pivot pin opening 48 receives a pivot pin 70 that is positioned along plane B and defines a pivot axis P-P for the wings 50 of the instrument 10.

In embodiments, the instrument 10 includes a biasing member 72 that is disposed within the gap 47 between the tines 46a, 46b of the wing support 46 and receives the pivot pin 70. The biasing member 72 may be in the form of a torsion spring having a loop 73 and arms 74a, 74b. The loop 73 is configured to receive the pivot pin 70 and each of the arms 74a, 74b is configured to engage a respective wing 50 to bias the wings 50 towards an open position (FIG. 1) as detailed below.

Each wing 50 has a body 51, a blunt tip 55, and a pivot support 56. Each pivot support 56 defines a pin opening 58 that is configured to receive the pivot pin 70 such that the wings 50 are pivotable about the pivot axis P-P between the open position (FIG. 1) and a closed position (FIG. 2). The body 51 defines a longitudinal suture slot 52 formed in an outer surface of the body 51 and a biasing slot 53 in an inner surface of the body 51. In addition, the body 51 defines a needle slot 96 adjacent the blunt tip 55. The biasing slot 53 of each wing 50 receives a respective arm 74a, 74b of the biasing member 72 such that the biasing member 72 urges the bodies 51 of the wings 50 towards the open position (FIG. 1).

Referring back to FIGS. 1 and 2, the port site closure instrument 10 is prepared for a surgical procedure by threading a suture 80 through the port site closure instrument 10 as detailed below. The suture 80 may be threaded through the port site closure instrument 10 by the manufacturer and sealed within a kit or may be prepared by a clinician before or during a surgical procedure. To thread the suture through the port site closure instrument 10, a first end 81a of the suture 80 is passed through a proximal suture aperture 22 such that the first end 81*a* exits from one of the distal suture apertures 42. It will be appreciated that the first end 81*a* of the suture 80 will pass through the suture channel 82 connecting the proximal suture aperture 22 with the distal suture aperture 42. From the distal suture aperture 42, the first end 81*a* of the suture 80 is passed through the opposite suture aperture 42 such that a loop 86 of the suture 80 is positioned around the wings 50.

With particular reference to FIG. 1, a first segment 86*a* of the loop 86 is positioned in the suture slot 52 of one wing 50 and a third segment 86*c* of the loop 86 is positioned in the suture slot 52 of the other wing 50 such that a second segment 86*b* of the loop 86 extends between the wings 50. The first end 81*a* of the suture 80 is then passed through the other suture channel 82 to exit the other proximal suture aperture 22. The suture 80 may be a barbed suture to allow the suture to move through tissue in a first direction and resist movement through tissue in a second opposite direction.

When the wings 50 are in the open position, the first and third segments 86*a*, 86*c* of the suture 80 are spaced apart from the distal portion 40 of the port site closure instrument 10 between the distal suture apertures 42 and the blunt tips 55 of the wings 50. In contrast, when the wings 50 are in the closed position, as shown in FIG. 2, the first and third segments 86*a*, 86*c* (only first segment 86*a* shown in FIG. 2) are positioned within the suture groove 84 and the suture slot 52 between the distal suture aperture 42 and the blunt tip 55.

Another method for threading the suture 80 through the port site closure instrument 10 may include forming the loop 56 about the wings 50 and sequentially or simultaneously passing the ends 81, 81*b* of the suture 80 through respective distal suture apertures 42 such that each end 81*a*, 81*b* exits from a respective one of the proximal suture apertures 22. It will be appreciated that a flexible needle (not shown) having a sharp or blunt tip may be used to thread the suture 80 through the port site closure instrument 10. In embodiments with a single suture channel 82 through the body 12 of the instrument 10, both ends 81*a*, 81*b* may be passed through the single suture channel 82 simultaneously.

With reference to FIGS. 6-12, a method of closing an incision in tissue with the port site closure system 1 including the port site closure instrument 10 detailed above is disclosed in accordance with the present disclosure. The incision may be provided for receiving a port during a surgical procedure. Initially, the port site closure instrument 10 is prepared by threading the suture 80 through the port site closure instrument 10 as described above. With the suture 80 threaded through the port site closure instrument 10, the ends 81*a*, 81*b* of the suture 80 are drawn proximally to transition the wings 50 from the open position to the closed position. Specifically, as the ends 81*a*, 81*b* are drawn proximally, the loop 86 is reduced about the wings 50 such that the wings 50 are moved against the bias of the biasing member 72 (FIG. 5) towards the closed position. Alternately, a clinician can manually move the wings 50 to the closed position and the suture 80 can be tensioned to retain the wings in the closed position.

Figure 7:
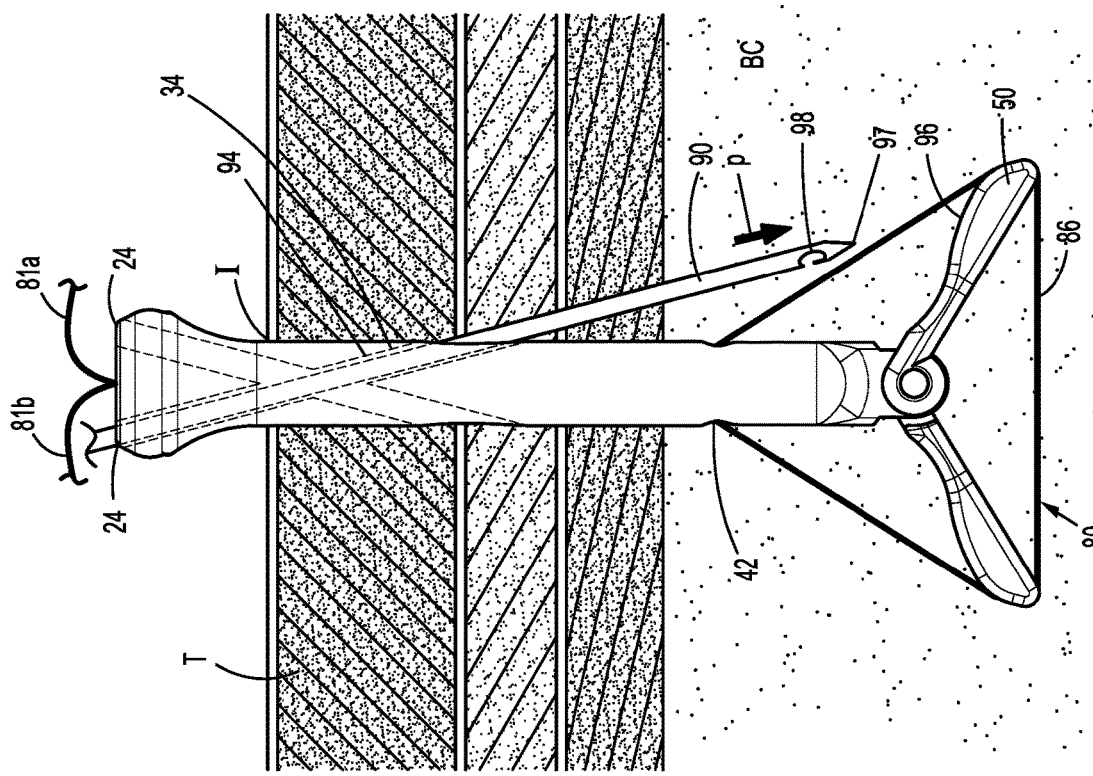
FIG. 7 is a side view of the port site closure instrument and suture of FIG. 6 positioned within the incision and extending into a body cavity with the wings in the open position and the suture positioned about the wings.

With the wings 50 in the closed position, the port site closure instrument 10 is passed through the incision such that the blunt tips 55 of the wings 50 atraumatically pass through tissue as shown in FIG. 6. The port site closure instrument 10 is passed through the tissue T until the distal suture apertures 42 are positioned within a body cavity BC and beyond the tissue T as shown in FIG. 7. When the distal suture apertures 42 are positioned within the body cavity BC, the wings 50 are allowed to transition to the open position. The ends 81*a*, 81*b* of the suture 80 can be released when the wings 50 are positioned within the incision, such that the tissue T maintains the wings 50 in the closed position until the wings 50 enter the body cavity BC beyond the tissue T. Alternatively, the ends 81*a*, 81*b* can be released after the wings 50 are received within the body cavity BC. The wings 50 and/or the suture 80 may draw the port site closure instrument 10 into the incision I as the wings 50 transition to the open position by interacting with an inner layer of the tissue T, e.g., the fascia layer/rectus sheath. When the wings 50 of the port site closure instrument 10 are positioned within the body cavity BC, the flange 21 of the proximal portion 20 may engage an outer layer of the tissue T to obstruct passage of the port site closure instrument 10 through the incision I. It will be appreciated that tension may be maintained in the suture 80 to keep the suture 80 taut but not enough tension to draw the wings 50 towards the closed position as shown in FIG. 6.

Figure 8:
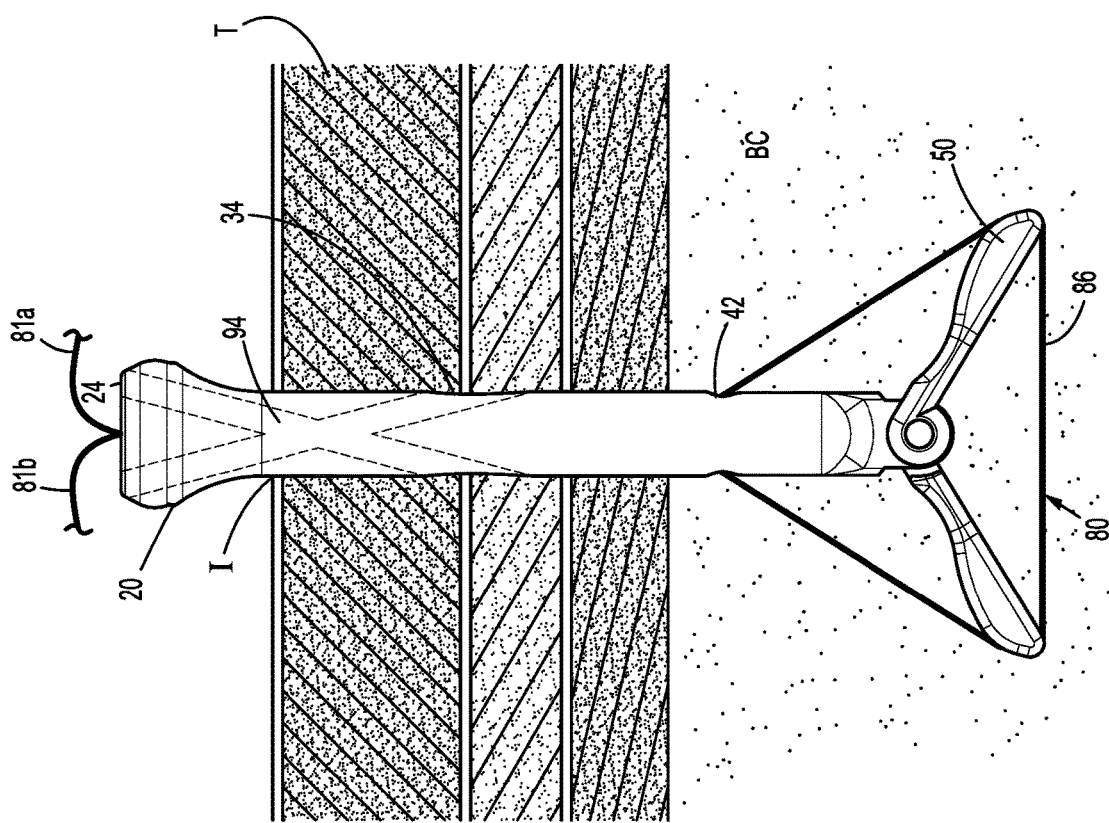
FIG. 8 is a side view of the port site closure instrument and suture of FIG. 7 with the needle passed through a first needle channel defined through the port site closure instrument.

Referring now to FIG. 8, when the port site closure instrument 10 is positioned within the incision I with the wings 50 in the open position, the distal needle apertures 34 are positioned between the inner and outer layers of the tissue T. The needle 90 is then passed through one of the proximal suture apertures 24 such that the needle 90 passes entirely through the needle channel 94 and through the tissue T. As the needle 90 passes through the tissue T, a sharp tip 97 of the needle 90 pierces the tissue T such that the needle 90 defines a path through the tissue T. It will be appreciated that the path through the tissue T passes through the innermost layer of the tissue T.

The needle channel 94 aligns the needle 90 with the loop 86 of the suture 80 such that as the needle 90 extends into the body cavity BC, the loop 86 of the suture 80 is captured within a hook 98 of the needle 90 as the needle 90 engages the suture 80. In the open position of the wings 50, the wings 50 position the loop 86 of the suture 80 away from the distal portion 40 of the port site closure instrument 10 such that a segment of the loop 86 is in the path of needle 90 when the needle 90 passes through the needle channel 94. In addition, when the wings 50 are in the open position, the needle slot 96 of each of the wings 50 is aligned with the path of the needle 90 to protect the sharp tip 97 of the needle 90 from making contact with tissue and/or organs within the body cavity BC. Further, when the sharp tip 97 of the needle 90 engages the needle slot 96 of a respective one of the wings 50, the needle 90 urges the wing 50 towards the open position and provides tactile feedback to a clinician that the needle 90 has engaged the wing 50.

As the needle 90 is moved in the direction indicated by the arrow M in FIG. 8, the needle 90 engages the suture loop 86 of the suture 80 as the needle 90 is pushed through the tissue T towards the wing 50. As the needle 90 is pushed towards the wing 50, the suture loop 86 may be captured within the hook 98 of the needle 90 or may slide along an outer surface of the needle 90. When the needle 90 engages the wing 50, the clinician may rotate needle 90 before withdrawing the needle 90 from the body cavity BC. Rotating the needle 90 may cause the loop 86 of the suture 80 to be captured within the hook 98 of the needle 90 as the needle 90 is withdrawn from the body cavity BC. The hook 98 of the needle 90 may be positioned such that when the tip 97 of the needle engages the needle slot 96 of one of the wings 50, the loop 86 of the suture 80 is positioned along the needle 90 at the hook 98.

Figure 10:
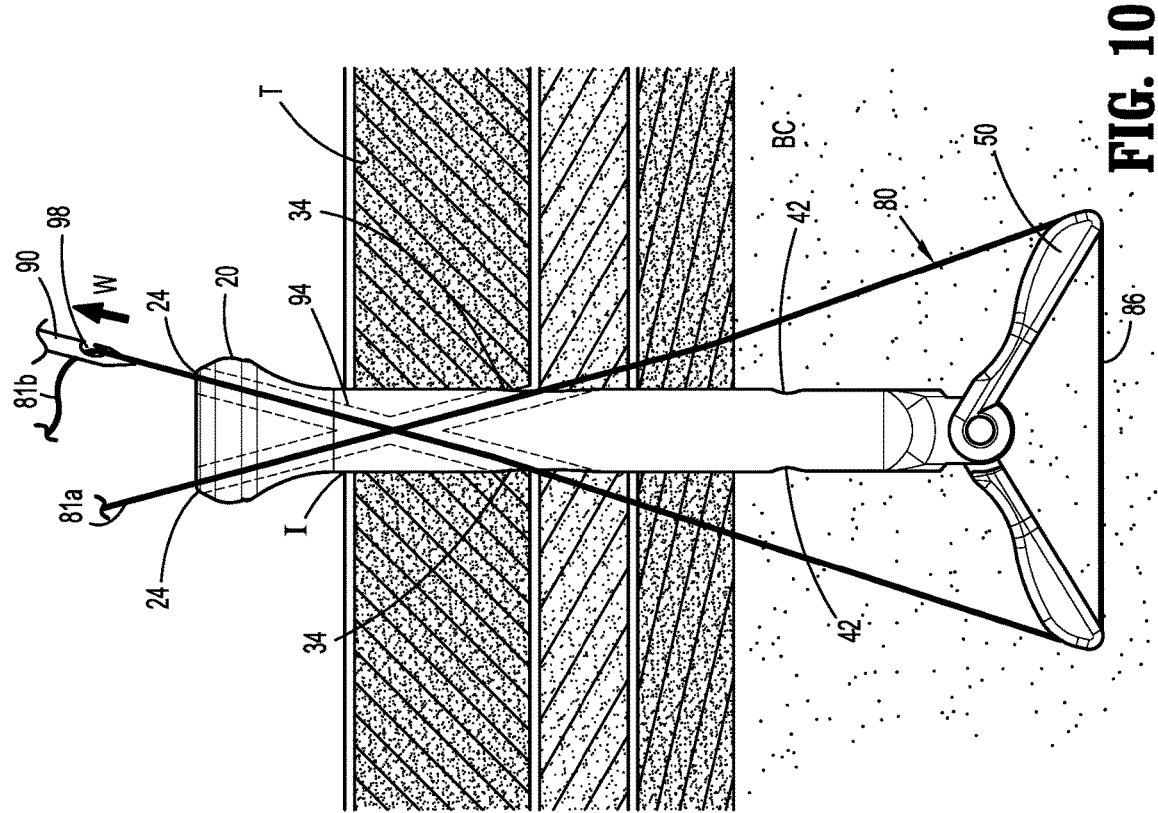
FIG. 10 is a side view of port site closure instrument and suture of FIG. 9 with the needle withdrawn from a second needle channel to draw a second end of the suture through a second needle channel of the port site closure instrument.
Figure 9:
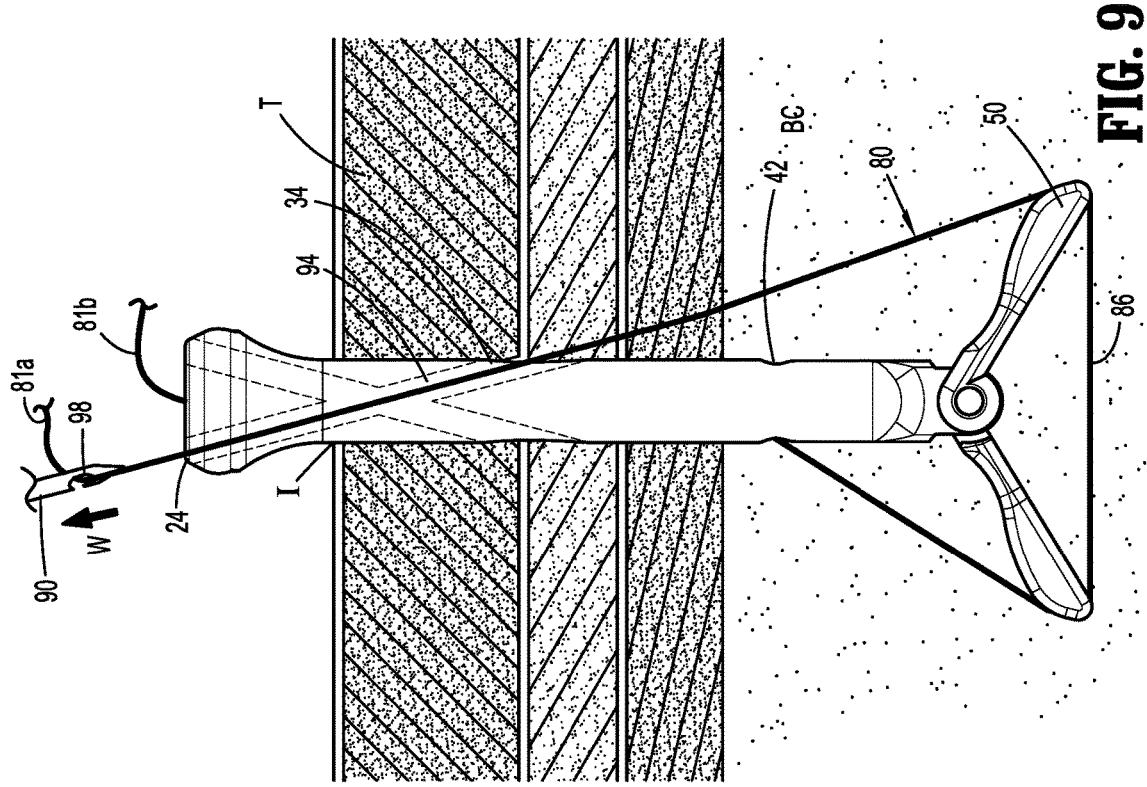
FIG. 9 is a side view of the port site closure instrument and suture of FIG. 8 with the needle withdrawn from the first needle channel and a first end of the suture extending from the first needle channel.

With reference to FIG. 9, the needle 90 is withdrawn from the body cavity BC in the direction indicated by arrow W. As the needle 90 is withdrawn with the loop 86 captured within the hook 98 of the needle 90, the end 81a of the suture 80 is released by the clinician such that the end 81a of the suture 80 can pass out of the distal suture aperture 42 and be drawn back through the tissue T and the needle channel 94 until the hook 98 with the captured suture 80 exits the proximal needle aperture 24. With the end 81a of the suture 80 passed through the tissue T, the needle 90 is passed through the other proximal needle aperture 24 and the tissue T to draw the other end 81b of the suture 80 through the tissue T in a similar manner to the end 81a detailed above such that the other end 81b exits the other proximal needle aperture 24 as shown in FIG. 10. It will be appreciated that the suture 80 is drawn through the tissue T on opposite sides of the incision I and passes through the inner-most layer of the tissue T.

Figure 11:
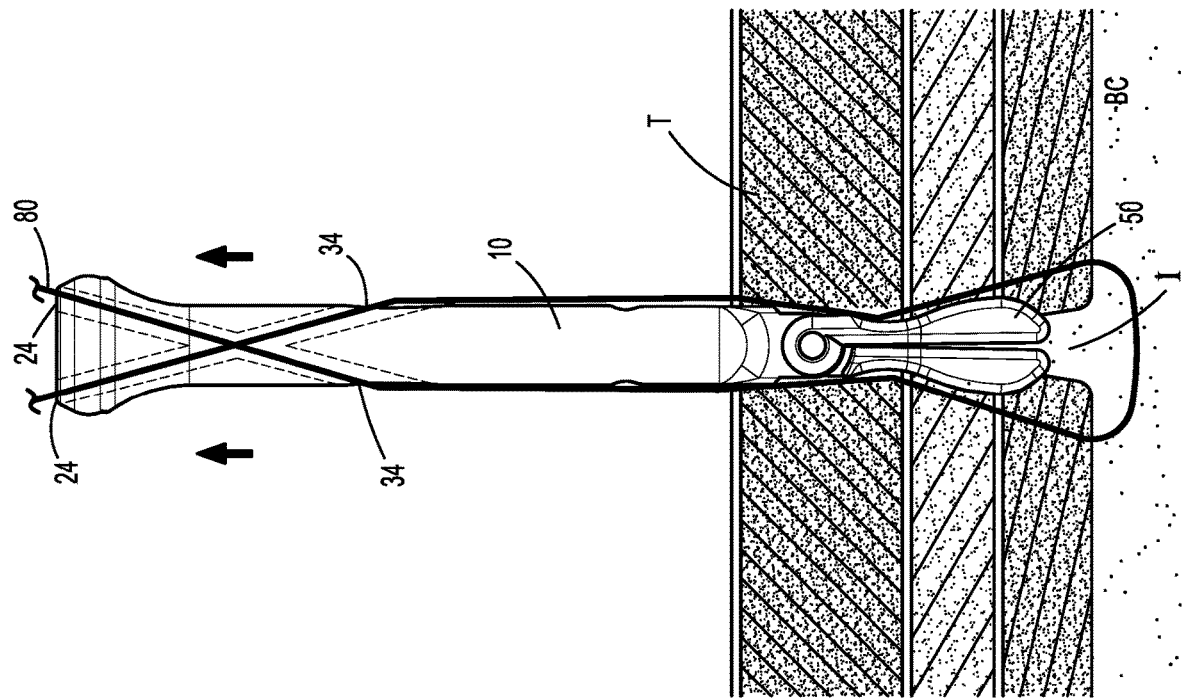
FIG. 11 is a side view of the port site closure instrument and suture of FIG. 10 with the port site closure instrument partially withdrawn through the incision in the tissue and the suture passed through an inside layer of the tissue.

When both ends 81a, 81b are drawn through the tissue T, the port site closure instrument 10 is withdrawn from the incision I as shown in FIG. 11. As the port site closure instrument 10 is withdrawn, the wings 50 engage the tissue T such that the wings 50 are moved against the biasing member 72 (FIG. 4) to move the wings 50 towards the closed position. In addition, as the port site closure instrument 10 is withdrawn, the loop 86 of the suture 80 remains within the body cavity BC.

The port site closure instrument 10 is withdrawn from the incision I until the distal needle apertures 34 are exposed on the outer side of the tissue T. When the distal needle apertures 34 are exposed, segments 86a, 86c of the loop 86 of the suture 80 are exposed between the distal needle apertures 34 and the incision I. The segments 86a, 86c of the suture 80 are grasped by the clinician and the ends 81a, 81b are released such that the ends 81a, 81b pass back through the port site closure instrument 10 and exit out of the distal needle apertures 34. Additionally or alternatively, the suture 80 may be cut adjacent the distal needle apertures 34 after the port site closure instrument 10 is withdrawn from the incision I.

Figure 12:
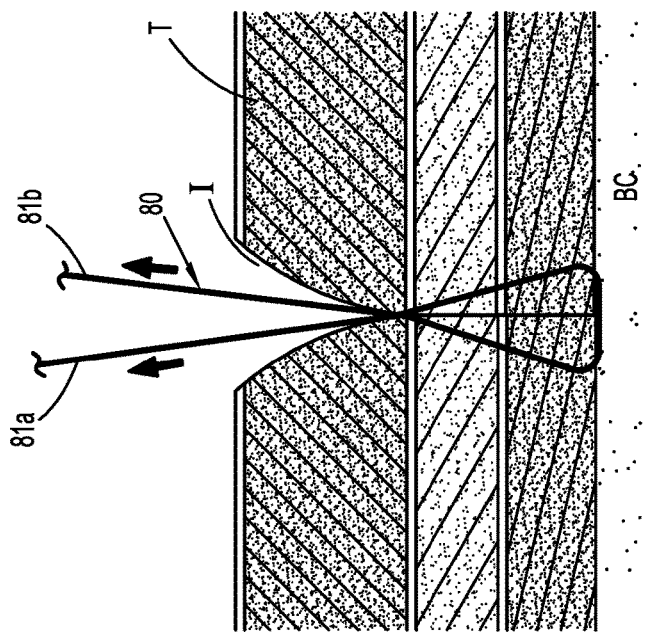
FIG. 12 is a side view of the incision after the port site closure instrument is fully removed from the incision with the suture withdrawn to close the incision in the tissue.

Referring now to FIG. 12, when ends 81a, 81b of the suture 80 outside of the port site closure instrument 10, the ends 81a, 81b are pulled away from the tissue T such that the segment 86b of the loop 86, that is positioned within the body cavity BC on an inside surface of the tissue T, draws the inside of the incision closed. The ends 81a, 81b can then be tied together to cinch the incision I closed.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A port site closure instrument comprising:
   a body defining a central longitudinal axis, a first plane, and a second plane perpendicular to the first plane, the first and second planes intersecting along the central longitudinal axis, the body having:
      a proximal portion defining a first proximal suture aperture, a first needle aperture, and a second needle aperture, the first and second needle apertures offset from the central longitudinal axis;
      a central portion defining a third needle aperture and a fourth needle aperture, a first needle channel defined through the body communicating the third needle aperture with the first needle aperture, a second needle channel defined through the body communicating the fourth needle aperture with the second needle aperture, the first and second needle channels positioned in the first plane; and
      a distal portion defining distal suture apertures in the first plane on opposite sides of the central portion, a first suture channel defined by the body communicating the distal suture apertures with the first proximal suture aperture; and
   a pair of wings pivotally supported by the distal portion of the body, the pair of wings is pivotable between an open position and a closed position, an outer surface of each of the wings defining a suture slot positioned along the first plane such that a suture exiting a respective one of the distal suture apertures and positioned in the suture slots is aligned with a respective one of the first or second needle channels.

2. The instrument according to claim 1, wherein each of the first and second needle channels is configured to receive a needle and to align the needle with the suture slot of a respective one of the wings.

3. The instrument according to claim 2, wherein each of the wings defines a needle slot proximal of the suture slot, the needle slot configured to receive a distal end of the needle and to protect the needle from extending through the wing when the wing is in the open position.

4. The instrument according to claim 1, wherein the pair of wings are biased towards the open position.

5. The instrument according to claim 1, wherein each wing of the pair of wings has a blunt tip configured to atraumatically contact tissue.

6. The instrument according to claim 1, further comprising a pivot pin passing through each of the wings and the distal portion of the body to pivotally couple the pair of wings to the distal portion.

7. The instrument according to claim 6, further comprising a torsion spring disposed about the pivot pin and engaged with each of the pair of wings to bias the pair of wings towards the open position.

8. The instrument according to claim 1, wherein the proximal portion of the body defines a second proximal suture aperture, a second suture channel defined by the body communicating the distal suture apertures with the second proximal suture aperture.

9. The instrument according to claim 8, wherein the first and second suture channels are on opposite sides of the central longitudinal axis proximal of the third and fourth needle apertures and form a common suture channel along the central longitudinal axis distal of the third and fourth needle apertures.

10. The instrument according to claim 1, wherein a segment of the first suture channel extends along the second plane and is offset from the central longitudinal axis proximal of the third and fourth needle apertures.

11. The instrument according to claim 10, wherein another segment of the first suture channel extends along the central longitudinal axis distal of the third and fourth needle apertures.

12. The instrument according to claim 1, wherein the distal portion includes a suture passage extending directly between the distal suture apertures and perpendicular to the central longitudinal axis.

13. The instrument according to claim 1, wherein the first and second needle channels intersect one another at the central longitudinal axis.

14. A port site closure system comprising:
a needle;
a suture having first and second ends; and
a port site closure instrument including:
 a body defining a central longitudinal axis, a first plane, and a second plane perpendicular to the first plane, the first and second planes intersecting along the central longitudinal axis, the body having:
  a proximal portion defining a first proximal suture aperture, a first needle aperture, and a second needle aperture, the first and second needle apertures offset from the central longitudinal axis;
  a central portion defining a third needle aperture and a fourth needle aperture, a first needle channel defined through the body communicating the third needle aperture with the first needle aperture, a second needle channel defined through the body communicating the fourth needle aperture with the second needle aperture, the first and second needle channels positioned in the first plane, the needle configured to slide through each of the first and second needle channels; and
  a distal portion defining distal suture apertures in the first plane on opposite sides of the central portion, a first suture channel defined by the body communicating the distal suture apertures with the first proximal suture aperture; and
 a pair of wings pivotally supported by the distal portion of the body, the pair of wings pivotable relative to one another between an open position and a closed position, an outer surface of each of the wings defining a suture slot positioned along the first plane, the suture passing through the first suture channel, exiting one of the distal suture apertures, and disposed within the suture slot of each of the wings such that the suture is aligned with a respective one of the first and second needle channels.

15. The system according to claim 14, wherein each of the first and second needle channels is configured to receive the needle and to align the needle with a portion of the suture extending between one of the distal suture apertures and a respective one of the suture slots.

16. The system according to claim 14, wherein the suture is configured to draw the pair of wings towards the closed position.

17. A method of closing an incision in tissue of a patient, the method comprising:

passing a distal portion of a port site closure instrument through the incision into a body cavity with a pair of wings coupled to the distal portion of the port site closure instrument in a closed position to position the pair of wings within a body cavity of the patient;
 allowing the pair of wings to transition to an open position within the body cavity with a proximal portion of the port site closure instrument positioned on an opposite side of the tissue from the distal portion of the port site closure instrument;
 passing a needle through a first needle channel of the port site closure instrument such that the needle captures a first portion of a loop of a suture disposed on the pair of wings and extending from a pair of distal suture apertures disposed on opposite sides of the distal portion of the port site closure instrument;
 withdrawing the needle to draw the first portion of the loop of the suture through the first needle channel;
 passing the needle through a second needle channel of the port site closure instrument such that the needle captures a second portion of loop of the suture;
 withdrawing the needle to draw the second portion of the loop of the suture through the second needle channel;
 removing the port site closure instrument from the incision; and
 drawing first and second ends of the suture proximally to close the incision.

18. The method according to claim 17, wherein passing the needle through the first needle channel includes the needle passing through tissue, including an inner-most layer of the tissue, between the port site closure instrument and the first portion of the suture, and wherein withdrawing the needle to draw the first portion of the loop of the suture through the first needle channel includes drawing the first portion of the suture and the first end of the suture through the tissue including the inner-most layer of the tissue.

19. The method according to claim 17, further comprising drawing the first and second ends of the suture proximally such that the suture holds the pair of wings in the closed position while passing the distal portion of the port site closure instrument through the incision into the body cavity.

20. The method according to claim 17, wherein allowing the pair of wings to transition to the open position within the body cavity includes releasing the first and second ends of the suture to allow the pair of wings to transition to the open position, the pair of wings biased towards the open position.

* * * * *